United States Patent
Osuka

(10) Patent No.: US 6,822,092 B2
(45) Date of Patent: Nov. 23, 2004

(54) EXPANDED PORPHYRINS AND A METHOD FOR SYNTHESIS THEREOF

(75) Inventor: Atsuhiro Osuka, Otsu (JP)

(73) Assignee: Japan Science and Technology Agency, Saitama (JP)

(*) Notice: Subject to any disclaimer, the term of this patent is extended or adjusted under 35 U.S.C. 154(b) by 0 days.

(21) Appl. No.: 10/275,694

(22) PCT Filed: May 23, 2001

(86) PCT No.: PCT/JP01/04327

§ 371 (c)(1),
(2), (4) Date: Nov. 8, 2002

(87) PCT Pub. No.: WO01/96344

PCT Pub. Date: Dec. 20, 2001

(65) Prior Publication Data

US 2003/0162963 A1 Aug. 28, 2003

(30) Foreign Application Priority Data

Jun. 12, 2000 (JP) ........................................ 2000-175309

(51) Int. Cl.⁷ ............................................. C07D 487/22
(52) U.S. Cl. ...................................... 540/472; 514/410
(58) Field of Search ........................... 540/472; 514/410

(56) References Cited

U.S. PATENT DOCUMENTS 5,883,246 A * 3/1999 Bruckner et al. ........... 540/145

FOREIGN PATENT DOCUMENTS

WO    WO-97/37995 A1 * 10/1997

OTHER PUBLICATIONS

Maria et al. Chem. Commun. 385–386, 1999.*

* cited by examiner

Primary Examiner—Richard L. Raymond
(74) Attorney, Agent, or Firm—Sherman & Shalloway

(57) ABSTRACT

Novel meso-aryl substituted expanded porphyrins comprising of alternate arrangement of more than six of pyrrole units bridged by a methine group whose hydrogen is substituted with Ar-group; and their synthetic method. Ar-group is either a 2,6-substituted phenyl group which can possess a substituent at the other 3, 4, and 5 positions, or 9-anthryl group which can possess a substituent at the other positions of the anthracence, or a cyclohexyl group which can possess a substituent at the other positions of the cyclohexyl group. The substituents at the 2 and 6 positions mentioned above can be selected independently from halogen atom or lower alkyl group of carbon number 1 to 4, substituents at 3–5 positions, 9-anthryl group and cyclohexyl group can be selected independently from the group consisting of substituted or non-substituted alkyl of carbon number 5 or 6, substituted or non-substituted aryl group, besides above mentioned substituents at 2 and 6 positions. Each Ar-group can be different.

5 Claims, 2 Drawing Sheets a          b

EXPANDED PORPHYRINS AND A METHOD FOR SYNTHESIS THEREOF

This application is a 371 of PCT/JP01/04327, filed May 23, 2001.

FIELD OF THE INVENTION

The present invention relates to novel expanded porphyrins that are macrocycles comprising of alternate arrangement of more than six of pyrrole units bridged by a methine group whose hydrogen is substituted with Ar-group (hereinafter "a methine carbon" will be called as C-1) at α position of the pyrrole, and further relates the easy synthetic method of these expanded porphyrins.

BACK GROUND OF THE INVENTION

In recent years, much attention has been paid to the exploration of chemistry of porphyrins and other tetrapyrrolic microcycles due to their high potential in a variety of fields. Similarly, expanded porphyrins that bear more than five pyrroles have attracted considerable attention in light of their promising properties. In contrast, there are only scattered reports on meso-aryl substituted expanded porphyrins that are structurally homologous to tetrakis-meso-aryl porphyrin in respect of alternate conjugative arrangement of pyrrole and methine carbon. Expected high potential of these meso-aryl expanded porphyrins stem from their characteristic interesting properties that are not found for porphyrins; namely, the larger cyclic n-network, red-shifted absorption bands, more flexible conformation of the macrocycles, and coordination ability of more than two metal ions.

Synthesis of expanded porphyrins with six pyrrole subunits were reported with trivial names of rubyrin (Sessler, J. L. et al., 1991) and hexaphyrin (Gossaurer, A., 1983). These compounds have attracted intense interests in light of the expected recognizing ability of particular tumor cells and the cell membrane permeability on the basis of the known properties of related porphyrins and thus a potential application as the stable drug delivery system. Further, expanded porphyrins, that are called as decaphyrin due to the constituent ten pyrrole subunits, were prepared and aroused a wide interest in their ability to form novel chelates with a variety of metals. Among them, a stable gadolinium Gd(III) decaphyrin has been demonstrated to be usable as a MRI diagnosis drug and several other metal complexes of decaphyrins are useful for photodynamic therapy owing to their red-shifted absorption bands. (WO96/21665, opened to the public on Jul. 18, 1996).

However, in these previous examples, the constituent pyrrole subunits are linked not with a methine C-1 subunit but sometimes linked directly. In this sense, meso-aryl expanded porphyrins that have a regular, alternate arrangement of a pyrrole and a methine C-1 subunit and thus can be regarded as real homologs of porphyrins with the name of "legitimate" expanded porphyrins are quite rare. There is no established procedure that allows the preparation of a series of meso-aryl expanded porphyrins.

Rothemund-Lindsey protocol has been used for effective preparation of porphyrins by treating an equimolar mixture of aryl aldehyde and pyrrole with acid catalyst in $CHCl_3$ or $CH_2Cl_2$ to form a equilibrated mixture of a cyclic porphyrinogen and linear oligomeric pyrromethene-oligomers that is subsequently oxidized to give a porphyrin and oligomeric tars. A typical synthetic procedure was reported by J. S. Lindsey et al. in Journal of Organic Chemistry vol 52, No.5 827–836 (1987), in which meso-tetraaryl and meso-tetraalkylporphyrins were prepared from the corresponding aldehyde and pyrrole with aid of boron trifluoride-etherate or trifluoroacetic acid as an acid catalyst and p-choranil as an oxidant.

Lindsey et. al. have reported that the yield of porphyrin by said synthesis method depends largely on the substrate concentrations, and under the certain acid concentration condition the porphyrin yield was reported to reach the maximum at the substrate concentration of ca. 10 mM, and at the substrate concentration of 1 mM or 100 mM, the yield of porphyrin has been reported to be reduced to approximately a half for the both cases. The reduction of the porphyrin yields at 1 mM or 100 mM concentrations has not been rationalized and any discrete products other than a porphyrin were not expected so far.

The object of the present invention is to establish a reliable synthetic method that allows the synthesis of a series of meso-aryl expanded porphyrins with the alternate arrangement of pyrrole subunit and a C-1 methine subunit in a cyclic manner. The another object is to provide a simplified method for preparation of meso-aryl expanded porphyrins comprising, forming a macrocycle by alternate bonding of more than 6 pyrrole units with methine whose hydrogen is substituted by Ar group at α position of the pyrrole. The inventor of the present invention found a very reliable synthetic procedure that allows the preparation of a series of meso-aryl expanded porphyrins. The inventor of the present invention has found that meso-aryl expanded porphyrins can be prepared from the Rothemund-Lindsey reaction of 2,6-disubstituted aromatic aldehyde and pyrrole under rather concentrated conditions at 6 times level. 9-Formylanthracene and cyclohexane carboaldehyde are also employed in this synthesis. Therefore it is now concluded that the above-mentioned objects are now accomplished.

DISCLOSURE OF THE INVENTION

The first one of the present invention is the finding of expanded porphyrins that are macrocycles comprising of alternate arrangement of more than six of pyrrole units bridged by a methine group whose hydrogen is substituted with Ar-group (hereinafter "a methine carbon" will be called as C-1) at α position of the pyrrole (wherein Ar is 2,6-substituted phenyl group which can possess a substituent at the 3, 4, or 5 position, a 9-anthryl group which can possess a substituent, or a cyclohexyl group which can possess a substituent. The said substituents at 2 and 6 positions can be selected independently from fluoro, chloro, bromo, iodo, lower alkyl group of carbon number 1 to 4, and lower alkoxy group, the said substituents at the 3–5 positions of Ar-group and those of 9-anthryl and cyclohexyl groups can be selected from the group consisting of substituted or non-substituted alkyl of carbon number 5 or 6, alkenyl group, alkynyl group, substituted or non-substituted aryl group, alkyl or aryl sulfonyl group, alkyl or aryl cyano group, cyano group, nitro group, amino group, carboxy group, carboalkoxy group or ester, amide and salt thereof and specific group having well-known target specific substrate besides above mentioned substituents at 2 and 6 positions. Each Ar-group can be different.

Favorably, the first one of the present invention is the novel expanded porphyrins forming a macrocycle by alternate bonding of more than 6 pyrrole units with methine whose hydrogen is substituted by Ar group at α position of pyrrole obtained by reacting pyrrole with 2,6 substituted benzaldehydes which can possess substituent at other position, 9-formylanthracenes which can possess substituent or cyclohexane carbaldehydes which can possess substituent under the presence of acid catalyst and by oxidizing with an oxidizing agent. More desirably, the first one of the present invention is the novel expanded porphyrins wherein aldehyde compound is selected from the group consisting of 2,6-difluorobenzaldehyde, 2,3,6-trifluorobenzaldehyde, 2,4,6-trifluorobenzaldehyde, 2,3,4,5,6-pentafluorobenzaldehyde, 2,6-dichlorobenzaldehyde, 2,3,6-trichlorobenzaldehyde, 2,4,6-trichlorobenzaldehyde, 2,3,4,5,6-pentachlorobenzaldehyde, 2,6-dimethylbenzaldehyde, 2,4,6-trimethylbenzaldehyde, cyclohexanecarbo aldehyde or 9-formylanthracenes, more favorably is the novel expanded porphyrins represented by following compounds selected from the group A forming a macrocycle by alternate bonding of more than 6 pyrrole units with methine whose hydrogen at α position of the pyrrole is substituted by Ar group at α position of pyrrole.

Compounds group A

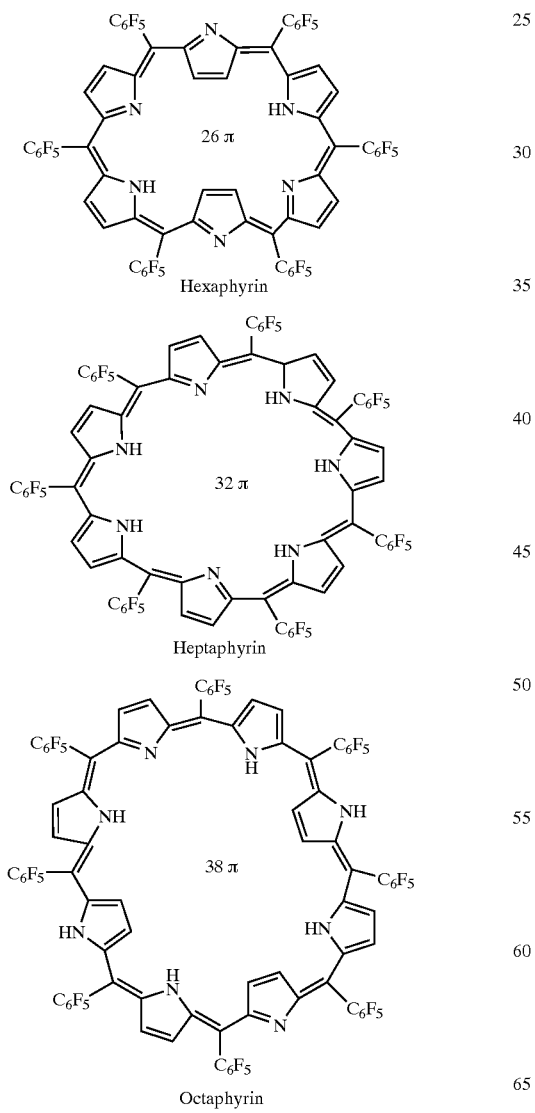

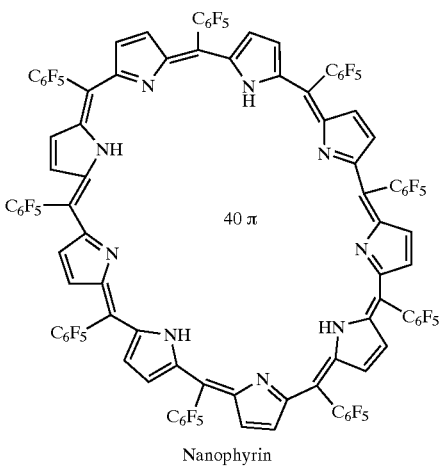

Nanophyrin

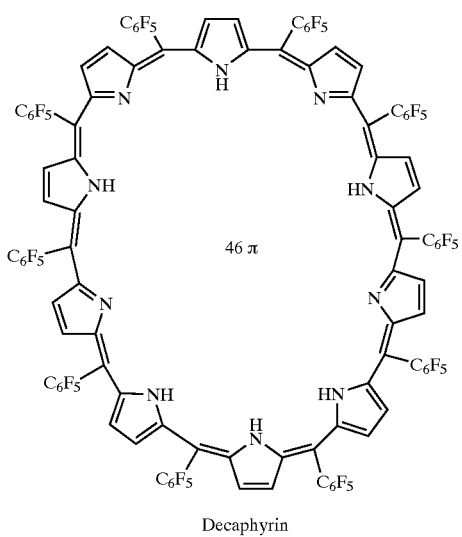

Decaphyrin

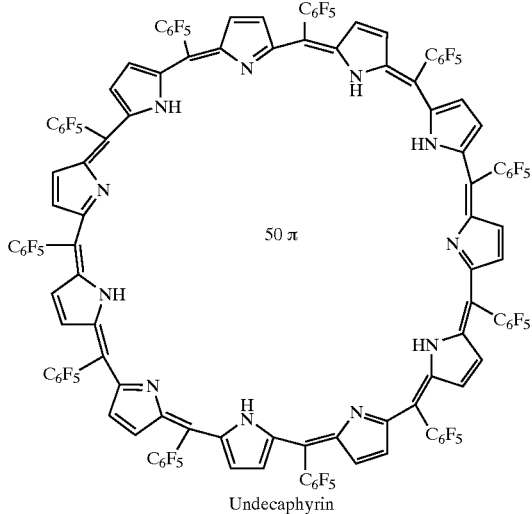

Undecaphyrin

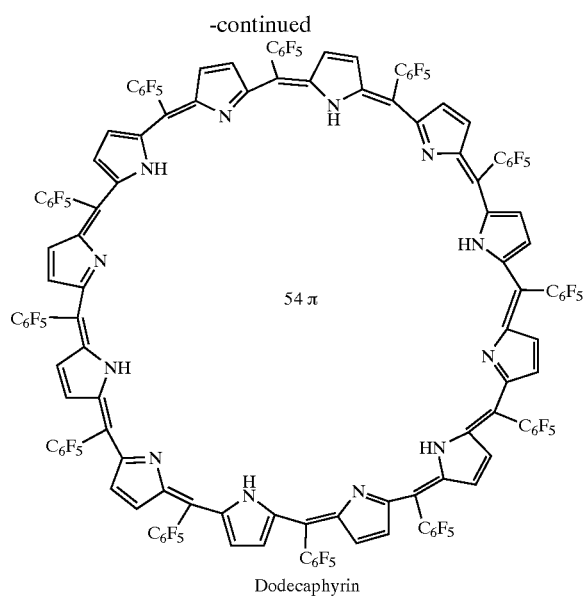
Dodecaphyrin (wherein Ar is 2,6-substituted phenyl group which can possess a substituent on 3, 4 or 5 position, 9-anthranil group which can possess a substituent or cyclohexyl group which can possess a substituent. And said substituent at 2 and 6 positions can be selected independently from the group consisting of fluoro, chloro, bromo, iodide, lower alkyl of carbon number 1 to 4 or lower alkoxy, substituent at 3–5 positions, 9-anthryl group and cyclohexyl group can be selected independently from the group consisting of substituted or non-substituted alkyl of carbon number 5 or 6, alkenyl group, alkynyl group, substituted or non-substituted aryl group, alkyl or aryl sulfonyl group, alkyl or aryl cyano group, cyano group, nitro group, amino group, carboxy group, carboalkoxy group or ester, amide and salt thereof and specific group having well-known target specific besides above mentioned substituents at 2 and 6 positions. Each Ar can be different).

These compounds are useful as an intermediate to obtain an useful compound for various uses through forming coordination compound with more than two metals or through exhibiting biological effects that are well-known for porphyrins or expanded porphyrins.

The second one of the present invention is the easy synthetic method of the expanded porphyrins that are macrocycles comprising of alternate arrangement of more than six of pyrrole units bridged by a methine group whose hydrogen is substituted with Ar-group. These expanded porphyrins are obtained by reacting pyrrole with 2,6 substituted benzaldehydes which can possess a substituent at other position, 9-formylanthracene which can possess substituent, or cyclohexane carboardehydes which can possess substituent under the presence of acid catalyst at the substrate concentration of larger than $6 \times 10^{-2}$ mol/L followed by oxidation with a suitable oxidant, (wherein Ar is either 2,6-substituted phenyl group which can possess a substituent on the other 3, 4, and 5 position, or a 9-anthryl group which can possess a substituent, or a cyclohexyl group which can possess a substituent. The said substituent at 2 and 6 positions can be selected independently from the group consisting of fluoro, chloro, bromo, iodide, lower alkyl of carbon number 1 to 4 or lower alkoxy, substituent at 3–5 positions, 9-anthranil group and cyclohexyl group can be selected independently from the group consisting of substituted or non-substituted alkyl of carbon number 5 or 6, alkenyl group, alkynyl group, substituted or non-substituted aryl group, alkyl or aryl sulfonyl group, alkyl or aryl cyano group, cyano group, nitro group, amino group, carboxy group, carboalkoxy group or ester, amide and salt thereof and specific group having well-known target specific besides above mentioned substituents at 2 and 6 positions. Each Ar can be different).

THE BEST EMBODIMENT TO CARRY OUT THE INVENTION

Figure 1:
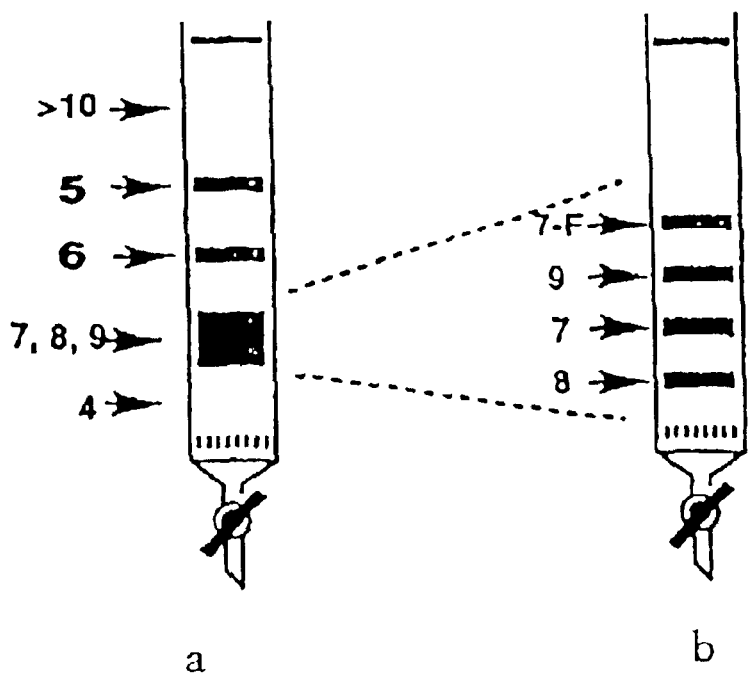
In FIGS. 1(a) is a silica gel column chromatography pattern for the products of example 1 using a 1:9 (v/v) mixture of ethyl acetate and n-hexane as an eluent and (b) is a silica gel column chromatography pattern for a mixture of octaphyrin (8), nonaphyrin (9), heptaphyrin (7), and fused heptaphyrin (7-F) with a 1:4 (v/v) mixture of $CH_2Cl_2$ and n-hexane as an eluent, which was used for the separation of these four expanded porphyrins.

The present invention will be illustrated more in detail according to the following description.

A. The important point of the expanded porphyrins of the present invention is that said expanded porphyrins is prepared by reacting pyrrole with 2,6 disubstituted benzaldehydes which can possess substituent at other position, 9-formylanthracenes which can possess substituent or cyclohexane carboaldehydes which can possess substituent under the presence of acid catalyst at substrate concentration of larger than $6 \times 10^{-2}$ mol/L followed by oxidation with a suitable oxidant Particularly, the expanded porphyrins forming a macrocycle by alternately bonding more than six pyrrole units with methine whose hydrogen at α position of the pyrrole is substituted by Ar group at α position of pyrrole is a novel expanded porphyrins, and the method for preparation is a simplified method which is accomplished by modifying methods for synthesis of conventional porphyrins, and has a merit that various kinds of expanded porphyrins can be obtained.

The substituents at the 2- and 6-positions of above mentioned 2,6 substituted benzaldehydes can be selected independently from the group consisting fluoro, chloro, bromo, iodo, lower alkyl of carbon number 1 to 4 or lower alkoxy. Further, the substituents at 3–5 positions of 2,6 substituted benzaldehydes, 9-anthranil group and cyclohexyl group are the substituents which are introduced at the step of starting material or after the synthesis of the expanded porphyrins, and usable substituents are mentioned as above. The expanded porphyrins of the present invention can be prepared by synthesizing expanded porphyrinogen reacting ArCHO (wherein Ar indicates the groups defined in the first one and second one of the present invention) with pyrrole by the condition enhancing these concentration (substrate concentration) higher than the concentration used in conventional Lindsey method under the presence of acid catalyst, then oxidizing said expanded porphyrinogen with an oxidizing agent. Trifluoroacetate (TFA) and trifluroroborane etherate ($BF_3OEt_2$) can be used as acid catalyst and p-chloranil or 2,3-dichloro-5,6-dicyano-1,4-benzoquinono (DDQ) can be as an oxidant. Dichloromethane ($CH_2Cl_2$), chloroform, carbon tetrachloride or mixture of these can be used as reaction solvent. Steric congestion surrounding a formyl group of aromatic aldehyde plays an crucial role for the production of expanded porphyrins, since with the following aromatic aldehydes (benzaldehyde, 2-chlorobenzaldhyde, 2-fluorobenzaldehye, 2-bromobenzaldehyde, 2-methylbenzaldehyde, 2,4-difluorobenzaldehyde, and 4-fluorobenzaldehyde) as a substrate, the formation od expanded porphyrins is very small, only negligible. In contrast, with sterically hindered aldehyde substrate such as 2,6-difluorobenzaldehyde, 2,6-dichlorobenzalde, 2,4,6-trifluorobenzaldehyde, 2,4,6-tribromobenzaldehyde, 9-formylanthracene, and 1-formylcyclohexane, expanded porphyrins were formed in substantial amounts.

B. Further, the inventor of the present invention have prepared 1-aryl-1,1-dipyrrylmethane (we call this as dipyrromethane) according to following scheme 1.

Scheme 1

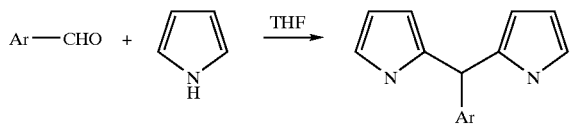

And it has been demonstrated that the porphyrins bearing even pyrrole units can be synthesized in a ring-size selective manner by the reaction of the dipyrromethane with aromatic aldehydes with aid of acid catalyst and the subsequent oxidation.

EXAMPLE

Example 1

In a 100 ml round-bottom flask, 2,3,4,5,6-pentafluorobenzaldehyde (494 μL, 4 mmole) and pyrrole (278 μL, 4 mmole) were dissolved in $CH_2Cl_2$ (60 mL), to which a solution of trifluoroborane etherate ($BF_3.OEt_2$) in $CH_2Cl_2$ (2.5 M, 100 μL) was added, and the resulting solution was stirred for 2 hours. Then, 2,3-dichloro-5,6-dicyano-1,4-benzoquinone (DDQ) (2.27 g, 10 mmol) is added and the resulting solution was stirred for one day. The reaction mixture was passed through a short alumina column, and the solvent was removed by a rotary evaporator. Expanded porphyrin products were separated over a silica gel column. Initially the column chromatography was carried with a 1:9 (v/v) mixture of ethyl acetate and n-hexane as an eluent, thus separating porphyrin (4), hexaphyrin (6), fused pentaphyrin (5), expanded porphyrins larger than decaphyrin (>10) from a mixture of heptaphyrin (7), fused heptaphyrin (7-HF), octaphyrin (8), and nonaphyrin (9), as shown in FIG. 1a. The last mixture was separated over a silica gel column with a 1:4 (v/v) mixture of $CH_2Cl_2$ and n-hexane as an eluent, giving pure heptaphyrin (7), fused heptaphyrin (7-HF), octaphyrin (8), and nonaphyrin (9), as shown in FIG. 1b. The yields, the molecular weights (m/e) determined by Fast Atom Bombardment Mass Spectroscopy (FAB MS), and the absorption bands (Soret-like bands and Q-like bands) are listed in Table 1.

TABLE 1

Porphyrins and expanded porphyrins obtained in Example 1

| N° | Estimated chemical formula | Yield % | Molecular wt.[1]: Calculated a Measured b | Soret (ε)[2] | Q & n-band |
|---|---|---|---|---|---|
| 4 | $C_{44}H_{10}N_4F_{20}$ | 11–12 | a: 974.0586<br>b: 974.0671* | 412.0 | 506.0, 537.0, 581.0 635.0 |
| 5 | $C_{55}H_{12}N_5F_{25}$ | 14–15 | a: 1217.0694<br>b: 1217.0762* | 466.5 (53961) 530.0 (53280) | 345.5 (27059) |
| 6 | $C_{66}H_{16}N_6F_{30}$ | 16–20 | a: 1462.0957<br>b: 1462.8453* | 566.5 (238510) | 711.5 (25799) 768.0 (88164) 881.0 (51758) |
| 7 | $C_{77}H_{16}N_7F_{34}$ | 4.4–5 | a: 1685.1<br>b: 1685 | 615.5 (86304) | 319.5 (40834) 393.0 (62581) |
| 8 | $C_{88}H_{22}N_8F_{40}$ | 5–6 | a: 1951.1<br>b: 1951 | 637.5 (11600) | 338.0 (49996) 407.5 (88834) |
| 9 | $C_{99}H_{25}N_9F_{45}$ | 2.5–3 | a: 2195.2<br>b: 2196 | 710.0 (89884) | 343.5 (45029) 444.5 (67050) |
| 10 | $C_{110}H_{25}N_{10}F_{50}$ | ~0.1 | a: 2436.15<br>b: 2436.7 | 747.5 | 491.0 |
| 11 | $C_{121}H_{28}N_{11}F_{55}$ | 0.1 | a: 2682.2<br>b: 2682 | 784 | 472.0 |

TABLE 1-continued

Porphyrins and expanded porphyrins obtained in Example 1

| N° | Estimated chemical formula | Yield % | Molecular wt.[1]: Calculated a Measured b | Soret ($\epsilon$)[2] | Q & n-band |
|---|---|---|---|---|---|
| 12 | $C_{132}H_{30}N_{11}F_{60}$ | 0.1 | a: 2923.7<br>b: 2923.5 | 829 | 435.0<br>493.0 |

N°unit number,
[1]Determined by FAB MS, and * is the high resolution mass data.
[2]the value on the parenthesis indicates the molecular extinction cofficient.

Example 2

To a solution of 2,3,4,5,6-pentafluorobenzaldehyde (2.5 mL, 20.3 mmol) and pyrrole (200 mL, 284 mmol), trifluoroacetate (TFA) (487.5 μL, 6.25 mmol) was added with stirring under the atmosphere of nitrogen and the resulting solution was stirred for 30 minutes. Reaction for dipyrromethane generation is shown in scheme 2.

Scheme 2

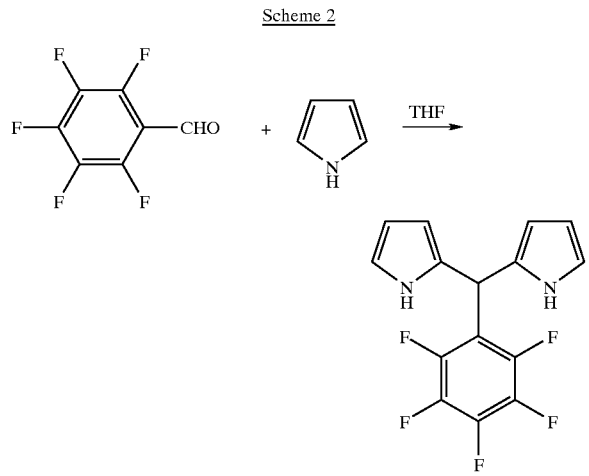

Figure 2:
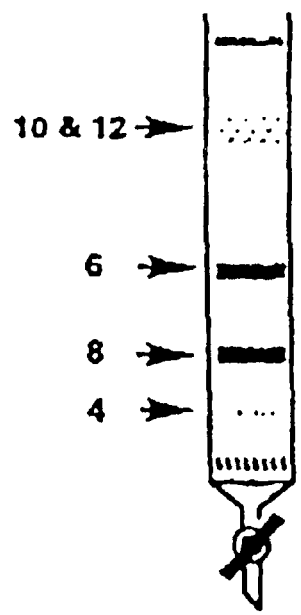
FIG. 2 is a column chromatography pattern showing the case of silica gel chromatography of the product of Example 2 using a solvent of ethyl acetate and n-hexane of 1:4 volume ratio. Expanded porphyrins of even number generate.

Then 200 mL of $CH_2Cl_2$ was added to the reaction mixture and diluted, then rinsed by NaOH aqueous solution. Solvent was removed using a rotary evaporator, and the dipyrromethane product was purified over a silica gel column to give 1-(2,3,4,5,6-pentafluoro-1,1,-(2-pyrryl)methane (6.16 g, 97%). The dipyrromethane (99 μL, 0.8 mmol) thus obtained and 2,3,4,5,6-pentafluoro-benzaldehyde (250 mg, 0.8 mmol) were dissolved in $CH_2Cl_2$ (20 mL) in a 50 mL round-bottom flask under nitrogen atmosphere and was added 20 μL of 2.5M trifluoroborane etherate ($BF_3OEt_2$). After 2 hours, DDQ (280 mg) was added and the solution was stirred for one day. The solvent was removed using a rotary evaporator and the expanded porphyrin products were separated by a column chromatography. As shown in FIG. 2, only the expended polyphyrins with even pyrrole subunits were formed and the separation process was facilitated significantly. Yields of the expanded porphyrins are shown in Table 2.

TABLE 2

Yields of expanded porphyrins in Example 2.

| N = unit numbers | Estimated chemical formula | Yield % |
|---|---|---|
| 4 | $C_{44}H_{10}N_4F_{30}$ | 20–23 |
| 6 | $C_{66}H_{16}N_6F_{30}$ | 25–28 |
| 8 | $C_{88}H_{22}N_8F_{40}$ | 15–18 |
| 10 | $C_{110}H_{26}N_{10}F_{60}$ | 2–3 |
| 12 | $C_{132}H_{30}N_{11}F_{60}$ | <1 |

Figure 3:
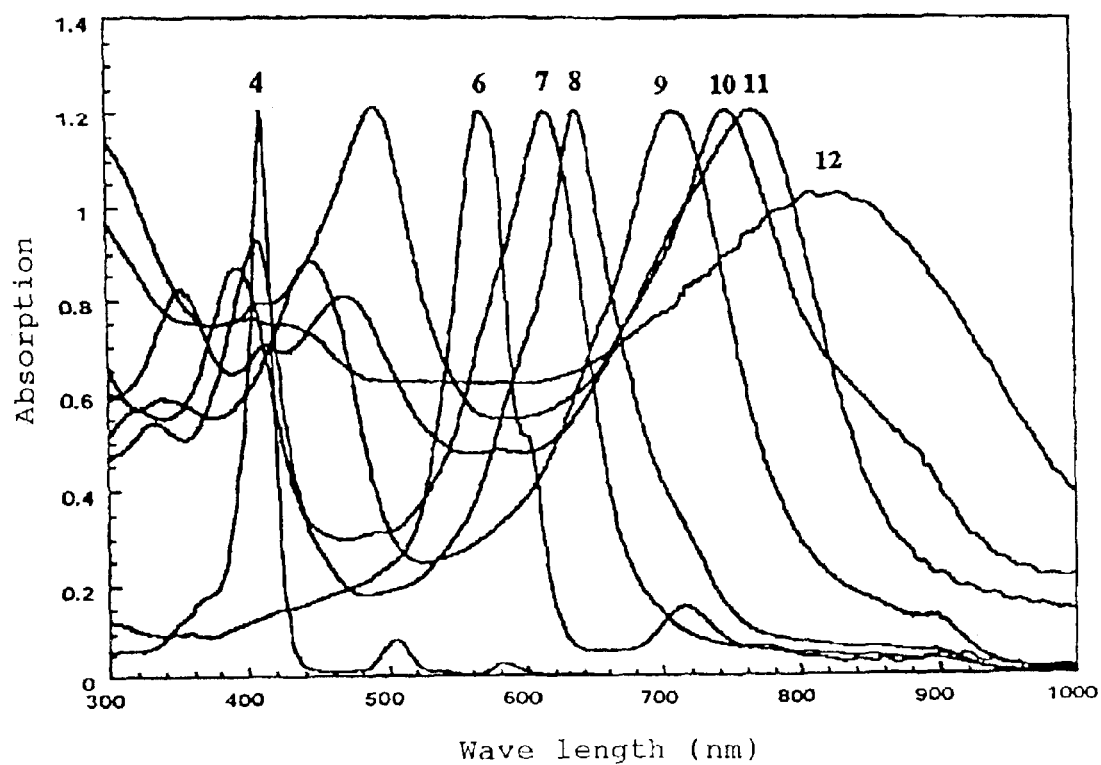
FIG. 3 shows the absorption spectra of expanded possessing 6–12 pyrrole units (respectively corresponding hexaphyrin, heptaphyrin, octaphyrin, nonaphyrin, decaphyrin, undecayphyrin, and doddecaphyrin). In all cases, the meso-Ar group is 2,3,4,5,6-pentaflurophenyl substituent.

FIG. 3 shows the absorption spectra of the expanded porphyrins synthesized in Examples 1 and 2 possessing 6–12 pyrrole units and Ar is 2,3,4,5,6-pentafluorophenyl.

Example 3

Essentially the same procedure as that of example 1 was repeated for the reaction of 2,6-dichlorobenzaldehyde (1.75 g, 10 mmol) and pyrrole (694 μL, 10 mmol) in $CH_2Cl_2$ (60 mL). In this experiment, the substrate concentrations of the substrates are both $1.7\times10^{-1}M$ that is higher than that used in Example 1. As is the same as in Example 1, the reaction mixture was passed through a short alumina column, and the solvent was removed by evaporation. By a silica gel column chromatography, the expanded porphyrin are separated with ethyl acetate as an eluant to give porphyrin (4), fused pentaphyrin (5), hexaphyrin (6), heptaphyrin (7), octaphyrin (8), nonphyrin (9), decaphyrin (10), undecaphyrin (11), and dodecaphyrin (12). The isolated yields and the molecular weights determined by FAB MS are listed in Table 3.

TABLE 3 porphyrins and expanded porphyrins of Example 3

| Pyrrole unit numbers | Estimated chemical formula | Molecular wt. Calculated Measured | Yield % |
|---|---|---|---|
| 4 | $C_{44}H_{22}Cl_8N_4$ | 890.3<br>890 | 10 |
| 5 | $C_{55}H_{25}Cl_{10}N_5$ | 1110.4<br>1110 | 18 |
| 6 | $C_{66}H_{32}Cl_{12}N_6$ | 1334.4<br>1333 | 8 |
| 7 | $C_{77}H_{39}Cl_{14}N_7$ | 1558.5<br>1569 | 3 |
| 8 | $C_{88}H_{44}Cl_{16}N_8$ | 1780.6<br>1781 | 4 |
| 9 | $C_{99}H_{51}Cl_{18}N_9$ | 2004.7<br>2003 | 2-0.3 |
| 10 | $C_{110}H_{55}Cl_{20}N_{10}$ | 2226.8<br>2225 | |
| 11 | $C_{121}H_{61}Cl_{22}N_{11}$ | 2448.8<br>2447 | |

TABLE 3-continued porphyrins and expanded porphyrins of Example 3

| Pyrrole unit numbers | Estimated chemical formula | Molecular wt. Calculated Measured | Yield % |
|---|---|---|---|
| 12 | $C_{132}H_{66}Cl_{24}N_{12}$ | 2671.0<br>2670 | |

Here it is worthy to note that a variety of metal ions can be put into the expanded porphyrins mentioned above. Such metal ions include Zn, Mg, Ca, Sr, Ba,.Sc, Y. La, Ce, Pr, Nd, Sm, Eu, Gd, Tb, Dy, Ho, Er, Tm, Yb, Lu, Ti, Zr, Hf, V, Nb, Ta, Th, U, Cr, Mo, W, Mn, Tc, Re, Fe, Ru, Os, Co, Rh, Ir, Ni, Pd, Pt, Cu, Ab, Au, Cd, Hg, Al, Ga, In, Ti, Si, Ge, Sn, Pb, As, Sb, and Bi.

As the specific group having well-known target specific, immunoglobulin or chip of immunoglobulin, steroid, sugar or T cell receptor can be mentioned.

POSSIBILITY FOR THE INDUSTRIAL USES

As mentioned above, the absorption bands (both the Soret-like bands and Q-like bands) of the expanded porphyrins are shifted to longer wavelength upon the increase in the number of the subunits and thus the macrocyclic sizes, and in a particular case of the dodecaphyrin, the Soret-like band appears at around 830 nm.

These expanded porphyrins are used as the novel optical materials such as a photodynamic therapy, an optical recording medium e.g. CD-R or DVD-R. These expanded porphyrins can coordinate one or more various metal ions, and the resultant metallated expanded porphyrins are useful for nuclear magnetic resonance imaging or radio imaging. Further these expanded porphyrins are also promising in light the their potential uses in reaction catalysts, since the cooperativity of several transition metals can be expected and the whole electronic properties of the expanded porphyrins can be tuned by two-electrons oxidation or reduction. As is evident in FIG. 3, the strong Soert-like absorption bands of decaphyrin (10), undecaphyrin (11), and dodecaphyrin (12) reach close at 800 nm, and these large macrocyclic molecules are almost transparent to the human's eye. These feature provide another merit for the expanded porphyrins, since these molecules can be used for information writing and reading out beyond the visible light range.

What is claimed is:

1. An expanded porphyrin forming a macrocycle by alternate bonding of 7 or more pyrrole units with methine whose hydrogen is substituted by Ar group at α position of the pyrrole,
   wherein Ar is 2,6-substituted phenyl group which can possess a substituent on 3, 4 or 5 position, 9-anthranyl group which can possess a substituent or cyclohexyl group which can possess a substituent;
   and said substituent at 2 and 6 positions of the phenyl group can be selected from fluoro, chloro, bromo, iodo, lower alkyl of carbon number 1 to 4 or lower alkoxy;
   substituent at 3–5 positions, 9-anthranyl group and cyclohexyl group can be selected independently from the group consisting of substituted or non-substituted alkyl of carbon number 5 or 6, alkenyl group, alkinyl group, substituted or non-substituted aryl group, alkyl or aryl sulfonyl group, alkyl or aryl cyano group, cyano group, nitro group, amino group, carboxy group, carboalkoxy group or ester, amide and salt thereof besides above mentioned substituents at 2 and 6 positions; and
   substituent of each Ar can be selected independently from the substituent mentioned above.

2. The expanded porphyrin of claim 1, wherein said expanded porphyrin forms a macrocycle by alternate bonding of 7 or more pyrrole units with methine whose hydrogen is substituted by Ar group at α position of the pyrrole obtained by reacting pyrrole with 2,6 substituted benzaldehydes which can possess being selected from the group consisting of 2,6 substituted benzaldehydes which can possess substituent at other position, 9-formylanthracenes which can possess substituent or cyclohexane carboaldehydes which can possess substituent.

3. The expanded porphyrin of claim 2, wherein aldehyde compound is selected from the group consisting of 2,6-difluorobenzaldehyde, 2,3,6-trifluorobenzaldehyde, 2,4,6-trifluorobenzaldehyde, 2,3,4,5,6-pentafluorobenzaldehyde, 2,6-dichlorobenzaldehyde, 2,3,6-trichlorobenzaldehyde, 2,4,6-trichlorobenzaldehyde, 2,3,4,5,6-pentachlorobenzaldehyde, 2,6-dimethylbenzaldehyde, 2,4,6-trimethylbenzaldehyde, cyclohexanecarboaldehyde and 9-formylanthracenes.

4. The expanded porphyrin according to claim 1, wherein the expanded porphyrin is the compound represented by following compounds group A which forms a macrocycle by alternate bonding of more than 6 pyrrole units with methine whose hydrogen is substituted by Ar group at α position of the pyrrole, compounds group A

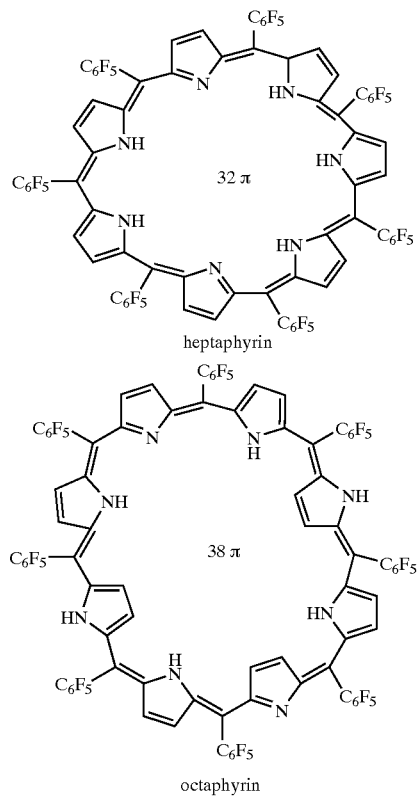

heptaphyrin octaphyrin

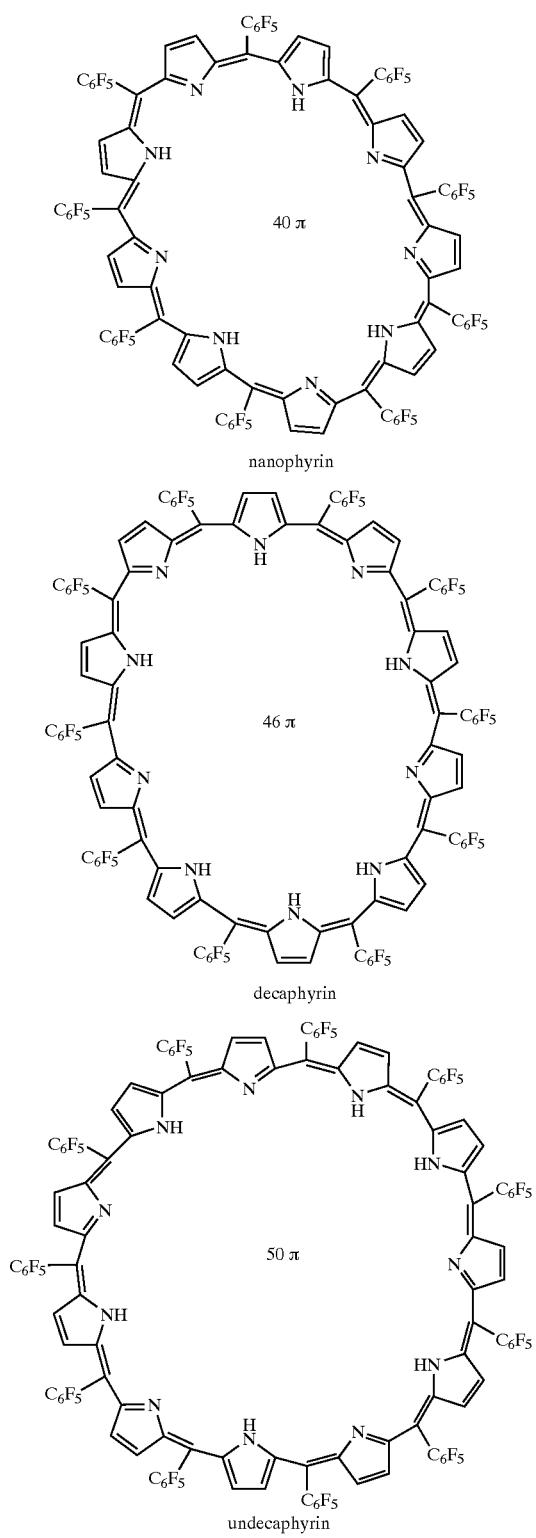

nanophyrin decaphyrin

50 π undecaphyrin

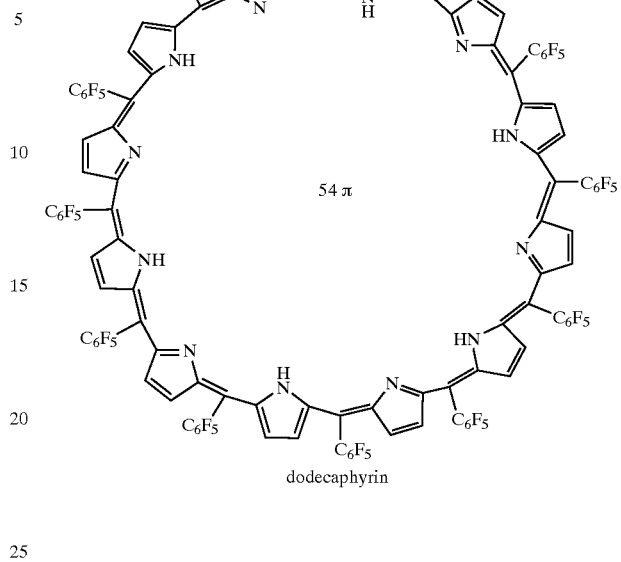

dodecaphyrin

5. A method for preparation of the expanded porphyrin forming a macrocycle by alternate bonding of more than 6 pyrrole units with methine whose hydrogen is substituted by Ar group at α position of the pyrrole obtained by reacting pyrrole with 2,6 substituted benzaldehydes which can possess substituent at other position, 9-formlyanthracenes which can possess substituent or cyclohexane carboaldehydes which can possess substituent under the presence of acid catalyst at substrate concentration of larger than $6 \times 10^{-2}$ mol/L and by oxidizing with an oxidizing agent, wherein Ar is 2,6-substituted phenyl group which can possess a substituent on 3, 4 or 5 position, 9-anthranyl group which can possess a substituent or cyclohexyl group which can possess a substituent; and said substituent at 2 and 6 positions of the phenyl group can be selected from fluoro, chloro, bromo, iodo, lower alkyl of carbon number 1 to 4 or lower alkoxy;

substituent at 3–5 positions, 9-anthranyl group and cyclohexyl group can be selected independently from the group consisting of substituted or non-substituted alkyl of carbon number 5 or 6, alkenyl group, alkinyl group, substituted or non-substituted aryl group, alkyl or aryl sulfonyl group, alkyl or aryl cyano group, cyano group, nitro group, amino group, carboxy group, carboalkoxy group or ester, amide and salt thereof besides above mentioned substituents at 2 and 6 positions of the phenyl group; and substituent of each Ar can be selected independently from the substituent mentioned above.

* * * * *